United States Patent [19]

Bordt et al.

[11] Patent Number: 6,074,651
[45] Date of Patent: Jun. 13, 2000

[54] VACCINE BASED ON TGEV FOR PROTECTION OF CANINES AGAINST CANINE CORONAVIRUS

[75] Inventors: Dale Bordt; Hans Draayer, both of White Hall, Ill.

[73] Assignee: Pfizer, Inc., New York, N.Y.

[21] Appl. No.: 09/281,243

[22] Filed: Mar. 30, 1999

Related U.S. Application Data

[62] Division of application No. 07/677,620, Mar. 27, 1991, Pat. No. 5,911,999, which is a continuation of application No. 07/243,252, Sep. 14, 1988, abandoned.

[51] Int. Cl.[7] .......................... A61K 39/155; A61K 39/12
[52] U.S. Cl. ...................... 424/211.1; 424/818; 424/819; 435/235.1; 435/325; 435/173.3
[58] Field of Search ................................ 424/211.1, 818, 424/819; 435/235.1, 325, 173.3

[56] References Cited

FOREIGN PATENT DOCUMENTS 1058340  2/1967  United Kingdom .

OTHER PUBLICATIONS

Draghici et al. Lucr. Inst. Cercet. Vet. Bioperp. "Pasteur", 1978, vol. 14, pp. 31–37, abstract only.

Murata, A., et al., Chem. Abs. 107:26455u (1987), and Agric. Biol. Chem., 51(3), 933–4 (1987).

Woods, R.D., et al., Biological Abs., 82:53821 (1986) and Amer. J. Vet. Res., 47(6):1239–1242 (1986).

Garwes, D.J., et al., Biological Abs., 72:14141 (1981) and J. Gen Virol., 52(1);153–158 (1981).

*Primary Examiner*—Ali Salimi
*Attorney, Agent, or Firm*—Hopgood, Calimafde Kalil & Judlowe, LLP

[57] ABSTRACT

A method for preventing canine coronavirus in dogs is disclosed which comprises administering to a dog a live or inactivated vaccine prepared from transmissible gastroenteritis virus of swine (a TGEV vaccine). An inactivated vaccine composition for use in such a method and a process for the manufacture of the inactivated vaccine composition are described.

6 Claims, No Drawings

VACCINE BASED ON TGEV FOR PROTECTION OF CANINES AGAINST CANINE CORONAVIRUS

This application is a division of application Ser. No. 07/677,620, filed Mar. 27, 1991, now U.S. Pat. No. 5,911,999, which is a continuation of application Ser. No. 07/243,252, filed Sep. 14, 1988 now abandoned.

This invention relates to vaccines and in particular to vaccines which are useful in protecting dogs against canine coronavirus.

The coronaviruses were first recognised and morphologically defined as a group by Tyrrell and co-workers. A comprehensive review of the biology and pathogenesis of coronaviruses has been published by H. wege et al., *Current Topics in Microbial Immunology,* 1982, 99, 165–200.

Canine coronavirus (CCV) was first isolated in 1971, and has increasingly become a problem, particularly amongst puppies and in kennel-raised dogs. It produces a mild to moderate diarrhea, often preceded by lethargy, depression and lack of appetite. Dehydration and subsequent weight loss generally follow. Although the disease is generally not fatal, it is felt that few puppies achieve their full vitality following the infection.

One treatment that may be used to overcome the effects of CCV infection involves giving massive doses of fluids to replace those lost, plus antibiotics to help control any opportunistic bacterial infection which can strike the dog in its weakened condition. Such treatment is expensive and suffers from the disadvantage that it is not preventative and is only useful to treat the infection after it has occurred.

A live vaccine introduced in 1983 by Fort Dodge Laboratories, Iowa, intended to protect dogs against CCV was soon demonstrated to be unsafe and was voluntarily withdrawn from the market in the same year (see M. L. Martin in *The Compendium on Continuing Education,* 1985, 12, 1012–1017).

An inactivated vaccine to protect dogs from CCV has now been introduced by Fort Dodge Laboratories under the trade name Duramune Cv-K. United States patents relevant to this product are U.S. Pat. No. 4,567,042 and U.S. Pat. No. 4,567,043.

In view of the contagious nature of CCV, and the economic aspects of the disease, new and improved vaccines are still urgently required.

It is known that canine coronavirus (CCV), transmissible gastroenteritis virus of swine (TGEV), feline infectious peritonitis virus (FIPV) and human respiratory coronavirus of the 229E group constitute an antigenic cluster of viruses within the family Coronaviridae (see N. C. Pedersen et al., *Arch. Virol.,* 1978, 58, 45–53 and S. Siddell et al., *J. Gen. Virol,* 1983, 64, 761–76).

However cross-protection studies with these viruses have met with little or no success. For example, in one study, pigs given virulent CCV did not produce neutralizing antibodies for TGEV (L. N. Binn et al., *Proceedings of the Annual Meeting U.S. Animal Health Association,* 1974, 78, 359–366), whilst in another study cats inoculated with a virulent field isolate of CCV were not protected against a challenge dose of FIPV (J. E. Barlough et al., *Laboratory Animal Science,* 1984, 34, 592–597).

Other work has shown that cats vaccinated with virulent TGEV and then challenge exposed with virulent FIPV were not protected against FIPV infection (see, for example, D. J. Reynolds and D. J. Garwes, *Arch. Virol,* 1979, 60, 161–166; and R. D. Woods and N. C. Pedersen, *Vet. Microbiol* 1979, 4, 11–16).

Surprisingly, it has now been found that vaccines based on TGEV protect the dog against CCV infection.

Accordingly, the present invention provides a method of preventing canine coronavirus infection in dogs, which method comprises administering to a dog a vaccine prepared from transmissible gastroenteritis virus of swine (a TGEV vaccine).

The invention also provides the use of transmissible gastroenteritis virus of swine for the manufacture of a vaccine for preventing canine coronavirus infection in dogs.

The TGEV vaccine may be live or inactivated.

A vaccine composition comprising inactivated TGEV forms another aspect of the present invention.

The invention also provides a process for preparing an inactivated vaccine composition, which process comprises admixing inactivated transmissible gastroenteritis virus of swine with a pharmaceutically acceptable carrier.

The TGEV vaccine for use in the method of the invention may be manufactured from an isolate of TGE virus, for example from the cell culture-adapted attenuated TGE virus known as Purdue strain TGE virus which has been deposited with the American Type Culture Collection and has ATCC Deposit No. VR-763.

Attenuated live TGEV suitable for use in the present invention may be prepared by passing the isolate of TGE virus in cells of porcine origin and/or feline origin several times, for example between 2 and 9 times, at a virus to cell ratio of 1:1 to 1:10,000, preferably about 1:100.

Preferably the cells of porcine origin comprise pig kidney (PK) cells, for example PK TC/115, and PK 15 (ATCC CCL 33) cell lines.

Preferably the cells of feline origin comprise feline kidney cells, especially Crandell feline kidney (CRFK) cells, (ATCC CCL 94).

The attenuated live TGE virus may be propagated by cell culture in a suitable culture medium using mammalian cells. The method includes the steps of inoculating mammalian tissue culture cells with TGEV (the cells normally having been cultivated into a 80–100% confluent monolayer prior to inoculation), harvesting the cells, typically between 1 and 7 days, preferably between 2 and 5 days, after inoculation, and collecting the propagated virus from the harvested cells.

Suitable culture media for use in the above process include those known in the art. A preferred culture medium in which the TGE virus may be propagated is Eagle's minimum essential medium (MEM) with or without serum.

Cell and virus growth is maintained under standard conditions, normally at 33–39° C., preferably at 35–38° C.

Virus fluids are suitably inoculated onto the mammalian cells at a virus to cell ratio of 1:1 to 1:10,000, preferably about 1:100. Preferably the virus culture medium is added after a 1 to 2 hour period.

The mammalian cells are suitably of porcine or feline origin, for example pig kidney (PK) cells, especially the PK 15 cell line (ATCC CCL 33), or feline kidney cells, especially Crandell feline kidney (CRFK) cells (ATCC CCL 94).

Preferably the mammalian cells are of feline origin, more preferably CRFK cells.

Virus fluids are preferably harvested about 3 days following inoculation by freeze-thaw or enzymatic action. The harvested virus fluids may conveniently be stored frozen.

Normally viral fluids harvested as described above contain at least $10^{3.5}$ infectious virus units/ml. When a live TGEV vaccine is required the virus fluids can be used with no further processing or they can be blended with a suitable stabilizer, for example N-Z amine-gelatin, sucrose phosphate glutamate (SPG), or sucrose phosphate glutamate albumin (SPGA). Normally the vaccine is desiccated. Preferably the post desiccation titre is at least $10^4$ per dose.

When an inactivated (or 'killed') vaccine is required, the harvested virus fluids may be inactivated by methods known in the art. Suitable methods include, for example, treatment with β-propiolactone formaldehyde, or ethyleneimine. After an inactivation and incubation period, the virus fluids may be tested for complete inactivation by known methods, for example by multiple passage on pig kidney cells.

A further, preferred, method for carrying out the inactivation step is to treat the harvested viral fluids with ascorbic acid and/or a salt thereof in the presence of oxygen and a source of heavy metal ions.

Suitable forms of ascorbic acid include the alkali metal or alkaline earth metal salts, for example the sodium, potassium or calcium salts, or ascorbic acid itself.

A preferred salt is the sodium salt.

A suitable ascorbate concentration for use in the inactivation step is in the range 1–10 mM, preferably 2.0 mM–6.0 mM, for example 2.5 mM.

Suitable sources of heavy metal ions include salts of copper, iron and zinc and mercury-containing compounds.

One preferred heavy metal ion is the cupric ($Cu^{2+}$) ion, a convenient source of which is cupric sulphate.

Another preferred heavy metal ion is mercury, convenient sources of which are organo-mercury compounds, especially ethylmercurithiosalicylic acid, sodium salt (thimerosal).

The heavy metal ion is present in a catalytic amount, a suitable concentration for use in the inactivation step being in the range 0.01 mM to 0.1 mM, preferably 0.015 mM to 0.05 mM, for example 0.022 mM.

The presence of oxygen is essential and it conveniently provided by adequate aeration.

Normally the inactivation step is allowed to proceed at between 1 and 54° C., preferably at about 37° C., until an inactivation test proves satisfactory. The required inactivation period is typically in the range 10–100 hours, generally about 48–72 hours.

For the inactivation of certain viruses, for example parvovirus and rotavirus, a second addition of ascorbic acid may be required to complete the inactivation process.

In addition, other agents known to inactivate viruses may optionally be added to complete the inactivation process. One such reagent is saponin as described in, for example, *Vet. Med. Nauki,* 1980, 17(3), 45–55 (A. Motovski et al.), which may, for example, be added at a concentration of 0.5 mg/ml about 72 hours after ascorbic acid addition. Such a procedure has proved especially useful for the inactivation of enveloped viruses such as viruses of the Herpes group including PRV and IBR.

The progress of the inactivation process may conveniently be monitored by measuring the viability of the virus at intervals using any convenient method, for example by indirect fluorescent antibody test to determine residual virus titre.

For the preparation of inactivated TGEV vaccine the inactivation step is normally carried out by adding appropriate quantities of stock solutions of sodium ascorbate and cupric sulphate to the bulk virus and mixing the resulting solution in the presence of air for about 72 hours at 37° C. After cooling to 4° C., a test of inactivation may conveniently be run using an appropriate cell culture such as PK or CRFK.

The TGEV vaccine for use in the method of the invention may optionally contain additional attenuated modified live virus or killed viruses such as canine distemper virus, canine parainfluenza virus, canine adenovirus (I and II), canine parvovirus and be combined with various inactivated bacterial vaccines such as Leptospira canicola-ictero bacterin, or canine Bordatella bacterin.

The inactivated TGEV vaccine composition of the invention may also optionally contain adjuvants including aluminium hydroxide (for example 2–25%, preferably, 5–25%, by weight), saponin (for example 0.5–1.5 mg/dose), and Freund's incomplete adjuvant (typical water in oil emulsion).

To prevent canine coronavirus infection in dogs, the TGEV vaccine may be administered parenterally (subcutaneously or intramuscularly) in a dose of at least 1.9 logs of virus particles per dose, preferably at least 1,000 virus particles (3 logs of virus particles) per dose. Advantageously the vaccine is administered in at least 4 logs of virus particles per dose.

The following Examples illustrate the invention.

EXAMPLES

In the examples described below, the following materials and methods were used.

A. TGE virus

Preparation A.1

Purdue strain TGE virus (ATCC VR-763) was passaged 4 times on pig kidney cells (designated PK0809) to produce a master seed virus. The experimental vaccines were derived from the master seed virus after 5 additional passages in the pig kidney cells.

Preparation A.2

The master seed virus from Preparation 1 was passaged 3 times in porcine kidney cells and twice in Crandell feline kidney cells (ATCC CCL 94).

B. Cell culture

Preparation B.1

The master seed virus was propagated at 35–38° C. on the pig kidney cell PK 15 cell line (ATCC CCL 33) in Eagle's MEM containing not more than 10% bovine serum.

Preparation B.2

The virus from Preparation A.2 was propagated at 35–38° C. on the Crandell feline kidney cell line (ATCC CCL 94) in Eagle's MEM containing not more than 10% bovine serum.

C. Virus growth

Preparation C.1

Two small roller bottles containing confluent PK0809 monolayers were inoculated with 1 ml of undiluted TGE master seed virus. After a 1–2 hour adsorption period the virus growth medium (Eagle's MEM containing not more than 2% bovine serum) was added and the virus was grown at 35–38° C.

Preparation C.2

Two small roller bottles containing confluent Crandell feline kidney cell (ATCC CCL 94) monolayers were inoculated with 1 ml of undiluted TGE master seed virus. After a 1–2 hour adsorption period the virus growth medium (Eagle's MEM containing not more than 2% bovine serum) was added and the virus was grown at 35–38° C.

Example 1

Modified Live TGEV vaccine

To one roller bottle containing TGE virus prepared as in Preparation C.1 above is added 17% N-Z amine-gelatin stabilizer. One freeze/thaw cycle is carried out and the resulting material is desiccated in 1 ml volumes and kept at 4° C. until required. The post desiccation titre should be at least $10^4$ per dose.

Example 2

Modified Live TGEV Vaccine

A modified live TGEV vaccine was prepared in the same way as in Example 1 except that the TGE virus prepared as in Preparation C.2 was used.

Example 3

Inactivated TGEV vaccines one roller bottle containing TGE virus prepared as in Preparation C.1 above was frozen and thawed (titre samples taken) and inactivated as follows (the bulk virus should have a pre-inactivation titre of at least $10^{5.5}$ per dose):

The bulk virus was put in a 1 liter glass bottle and brought to 37° C. Sodium ascorbate stock solution (1% w/v) and cupric sulphate stock solution (1.1% w/v) were then added to bring the final concentration of ascorbate to 5.05 mM and the final concentration of cupric ions to 0.022 mM. The contents of the bottle were mixed with adequate aeration for 72 hours at 37° C. and then cooled to 4° C. A test of inactivation was run in pig kidney cells.

After proof of inactivation, the bulk virus was split and adjuvanted to give two inactivated vaccines as follows:

Vaccine A

One half of the inactivated bulk virus was treated with 10% aluminium hydroxide by stirring for 15–20 hours at 4° C.

Vaccine B

The other half of the inactivated bulk virus was adjuvanted as follows:

Solution 1 consists of 5 ml emulsifier added to 95 ml of Drakoil 6 VR.

Solution 2 consists of 2.5 ml Tween 80 added to 47.5 ml of killed TCE virus.

Solution 1 (21 ml) is added to Solution 2 (7 ml) and mixed using a Perfektum emulsifying needle prior to vaccination.

Example 4

Modified live TGEV vaccine dose titration and CCV immunogenicity evaluation in dogs a) Experimental Design Four TGEV vaccine permutations were evaluated; two antigenic levels, each administered intramuscularly (IM) or subcutaneously (SC). Five dogs were assigned to each IM group and 4 dogs to each SC group. Five dogs were used as unvaccinated controls.

Dogs in each vaccine group received two 2 ml doses of a modified live TGEV vaccine administered IM or SC at a 4 week interval. Three weeks following the second vaccination, all dogs were challenged orally and intratonsilar with CCV. Three parameters were evaluated to determine the efficacy of each vaccine permutation: serologic response, rectal CCV shedding and CCV infection of intestinal epithelial cells 5 days following challenge.

b) Materials and Methods i) Animals

Twenty-three mixed breed dogs, 16–20 weeks old, with a history of no vaccination to CCV were used. Dogs were susceptible to CCV as indicated by CCV-IFA titers of <1:2.

ii) vaccine and vaccination

The TGEV master seed virus was passaged three times in porcine kidney cells and twice in Crandell feline kidney (CRFK) cells as described in Preparation A.2. The virus harvest material was held at −70° C. prior to use.

iii) Serology

Antibody titres were determined at the time of vaccination, challenge, and 5 days following challenge using an indirect fluorescent antibody test.

iv) Challenge

Field isolate designated CCV-6, and passaged once in CRFK was used. Dogs were deprived of feed for 24 hours prior to challenge. Four mls of virus harvest material was delivered to each dog in the following manner: 2 mls of virus material mixed with ¼ cup of Alpo™ was given orally. Dogs were then anesthetized with Prom Ace® (Ayerst Laboratories INC NY, N.Y. 10017) according to label recommendations, and 1 ml of CCV was then injected into each tonsil. Dogs were monitored on the day of challenge and for 5 days following challenge for gross clinical signs and rectal virus shedding.

v) Rectal Virus Recovery Following Challenge

Rectal swabs were collected daily and processed for virus isolation by passage in CRFK cells.

vi) Evaluation of Small Intestine Following CCV Challenge

Five days after CCV challenge, all dogs were necropsied and the entire small intestine was removed. Slide intestinal impressions were made from regularly spaced intestinal segments. The presence of CCV antigen was determined using an indirect fluorescent antibody test. Impression slides were scored according to the percentage of specific CCV-fluorescence observed.

c) Results

No clinical signs were observed among dogs following vaccination or challenge.

i) vaccine virus Titers

Antigenic levels used in this study were $10^{3.3}$ and $10^{2.3}$ TCID$_{50}$/dose.

ii) Serological Response

Serologic results are summarized in Table 1.

TABLE 1

| Reciprocal CCV Geometric Mean Antibody Titers | | | |
|---|---|---|---|
| TGE | Weeks Post 1st Vac | | 5D |
| Vaccine | 0 | 3 | 7 | PC |
| $10^{3.3}$ IM | <2 | 40 | 139 | 422 |
| $10^{3.3}$ SC | <2 | 24 | 113 | 320 |
| $10^{2.3}$ IM | <2 | 46 | 53 | 485 |
| $10^{2.3}$ SC | <2 | 34 | 24 | 190 |
| Non-Vac | <2 | <10 | <10 | <10 |

All dogs had no measurable antibody titre at the time of vaccination. Non-vaccinated controls remained less than 1:10 throughout the study indicating absence of extraneous CCV infection.

Dogs in all four vaccine groups ($10^{3.3}$ IM, $10^{3.3}$ SC, $10^{2.3}$ IM and $10^{2.3}$ SC) developed similar CCV geometric mean antibody titers (GMAT) within 3 weeks following the first vaccination (1:24 to 1:46) indicating a primary response from virus replication. Three weeks following the 2nd vaccination a dose response was demonstrated among dogs in $10^{3.3}$ IM and SC groups (GMAT 1:139 and 1:113) and the $10^{2.3}$ IM and SC groups (GMAT 1:53 and 1:24). All vaccinated dogs demonstrated an anamnestic response following CCV challenge; responses among dogs in groups $10^{3.3}$ IM and SC were 3-fold and responses among dogs in groups $10^{2.3}$ IM and SC were nine and eight-fold, respectively. The serology results indicate that the canine immune system, primed by the heterologous live TGEV vaccine responded anamnestically to homologous virulent CCV challenge.

Non-vaccinated dogs, 5 days after challenge, had no measurable antibody response.

iii) CCV Post-Challenge Evaluations

Duplicate titrations of CCV challenge virus indicated the dogs were challenged with $10^{5.4}$ TCID$_{50}$/ml ($10^{6.0}$ TCID$_{50}$/dose).

CCV virus isolations were monitored for 5 days following challenge. All dogs were free of CCV prior to challenge. CCV virus inclusions within CRFK cytoplasm were observed from all non-vaccinated controls (100% recovery) throughout the 5 day period. Among vaccinated dogs, CCV virus inclusions were not observed, indicating no virus recovery. Passage of material did not enhance virus recovery.

Table 2 summarizes average specific CCV intestinal fluorescence among groups and non-vaccinated controls.

TABLE 2

Average Score (%) of CCV Intestinal CCV by Immunofluorescence

| | Gut Impression Number (Duodenum to Ileum) | | | | | | | | |
|---|---|---|---|---|---|---|---|---|---|
| GROUP | 1.0 | 2.0 | 3.0 | 4.0 | 5.0 | 6.0 | 7.0 | 8.0 | TOTAL |
| 3.3 IM | 7.6 | 9.0 | 5.0 | 2.0 | 5.0 | 0.0 | 2.0 | 0.0 | 30.6 |
| 3.3 SC | 17.5 | 5.0 | 8.8 | 7.5 | 2.5 | 2.5 | 0.0 | 12.5 | 58.3 |
| 2.3 IM | 10.0 | 12.0 | 2.0 | 0.4 | 0.4 | 6.0 | 1.4 | 14.0 | 46.2 |
| 2.3 SC | 10.0 | 1.3 | 5.3 | 0.0 | 0.0 | 0.0 | 15.0 | 10.0 | 42.5 |
| Control | 46.0 | 82.0 | 24.0 | 40.0 | 35.0 | 48.0 | 40.0 | 12.0 | 327.0 |

Specific fluorescence for CCV as indicated by bright apple green fluorescence was observed along the entire length of the small intestine. All dogs showed some degree of CCV infection. A significant reduction in intestinal fluorescence, as compared to the controls, was observed amongst all the vaccinated dogs.

Average total scores between vaccine groups 5 days following CCV challenge were similar (30.6, 56.3, 46.2, 42.5) and the average total score of the non-vaccinated control dogs was considerably higher (327) than the vaccine groups.

d) Conclusion

Dogs among all vaccine groups developed similar antibody responses 3 weeks following the first vaccination. An antibody dose response was seen between dogs in the $10^{3.3}$ and $10^{2.3}$ vaccine groups 3 weeks following the second vaccination.

Following CCV challenge, virus was recovered from all non-vaccinates and CCV intestinal infection appeared active and widespread. Vaccinated dogs in all vaccine groups, however, demonstrated an active cellular immune response with no rectal virus shedding and apparently were protected from CCV challenge by TGE vaccine induced antibodies or cell mediated immunity.

What is claimed is:

1. A vaccine composition suitable for administration to a canine, said composition comprising inactivated transmissible gastroenteritis virus of swine (TGEV).

2. A process for manufacturing an inactivated vaccine prepared from transmissible gastroenteritis virus of swine (a TGEV vaccine), which process comprises:

(a) passing an isolate of TGE virus in cells of porcine and/or feline origin at a virus to cell ratio 2 of 1:1 to 1:10,000 to obtain an attenuated live TGE virus;

(b) propagating the live TGE virus by cell culture in mammalian cells;

(c) harvesting viral fluids so produced; and (d) inactivating the said viral fluids with a viral inactivating agent.

3. A process according to claim 2 in which the isolate of TGE virus is passed in cells of feline origin.

4. A process according to claim 2 in which the isolate of TGE virus is passed in Crandell kidney cells (ATCC CCL 94).

5. A process according to claim 2 in which the said viral fluids are inactivated with ascorbic acid and/or a salt thereof in the presence of oxygen and a source of heavy metal ions.

6. A process according to claim 5 in which the said viral fluids are inactivated with ascorbic acid and/or a salt thereof in the presence of oxygen and a source of heavy metal ions selected from the group consisting of salts of copper-, iron-, zinc-, and mercury-containing compounds, and compatible mixtures thereof.

* * * * *